United States Patent
Amano et al.

(10) Patent No.: US 8,139,224 B2
(45) Date of Patent: Mar. 20, 2012

(54) PARTICLE CONCENTRATION DETECTING DEVICE

(75) Inventors: Noriyasu Amano, Gamagori (JP); Rie Osaki, Anjyo (JP); Kazuki Matsuo, Okazaki (JP); Naoya Kato, Aichi-ken (JP); Hitoshi Uda, Toyota (JP)

(73) Assignees: Toyota Jidosha Kabushiki Kaisha, Aichi-Ken (JP); Nippon Soken, Inc., Aichi-Ken (JP)

( * ) Notice: Subject to any disclaimer, the term of this patent is extended or adjusted under 35 U.S.C. 154(b) by 289 days.

(21) Appl. No.: 12/669,165

(22) PCT Filed: Jul. 15, 2008

(86) PCT No.: PCT/JP2008/062751
§ 371 (c)(1),
(2), (4) Date: Jan. 14, 2010

(87) PCT Pub. No.: WO2009/014030
PCT Pub. Date: Jan. 29, 2009

(65) Prior Publication Data
US 2010/0208269 A1  Aug. 19, 2010

(30) Foreign Application Priority Data
Jul. 20, 2007  (JP) ................................. 2007-189584

(51) Int. Cl.
*G01N 21/00* (2006.01)
(52) U.S. Cl. .......................... 356/442; 356/432; 356/441
(58) Field of Classification Search ........... 356/432–444
See application file for complete search history.

(56) References Cited

U.S. PATENT DOCUMENTS

| | | | | |
|---|---|---|---|---|
| 4,037,973 A | * | 7/1977 | Carr | 356/435 |
| 4,066,362 A | * | 1/1978 | Carter | 356/409 |
| 4,451,152 A | * | 5/1984 | Topol et al. | 356/440 |
| 5,548,393 A | * | 8/1996 | Nozawa et al. | 356/70 |

FOREIGN PATENT DOCUMENTS

| | | |
|---|---|---|
| JP | 55-052932 A | 4/1980 |
| JP | 58-161850 A | 9/1983 |
| JP | 08-086751 A | 4/1996 |
| JP | 11-337487 A | 12/1999 |
| JP | 2000-206106 A | 7/2000 |
| JP | 2001-124764 A | 5/2001 |
| JP | 2006-349634 A | 12/2006 |

\* cited by examiner

*Primary Examiner* — Gregory J Toatley
*Assistant Examiner* — Jarreas C Underwood
(74) *Attorney, Agent, or Firm* — Sughrue Mion, PLLC

(57) ABSTRACT

A particulate concentration detector including a detection mechanism having a light emission unit and light reception unit. The particulate concentration detector detects the concentration of particulates suspended in a liquid from the light amount detected by the detection mechanism. The detection mechanism includes a first light guide, a second light guide, a liquid chamber, and a third light guide. The first light guide is arranged at a location facing toward a light emission surface of the light emission unit. The second light guide is arranged at a location facing toward a light reception surface of the light reception unit. The liquid chamber is formed between the first light guide and second light guide and allows the liquid to flow therein. The third light guide is arranged in an oscillatable manner in the liquid chamber so as to face toward the first light guide and the second light guide.

20 Claims, 5 Drawing Sheets

PARTICLE CONCENTRATION DETECTING DEVICE

CROSS REFERENCE TO RELATED APPLICATIONS

This application is a National Stage of International Application No. PCT/JP2008/062751, filed Jul. 15, 2008, which claims priority from Japanese Patent Application No. 2007-189584, filed Jul. 20, 2007, the contents of all of which are incorporated herein by reference in their entirety.

FIELD OF THE INVENTION

The present invention relates to a particulate concentration detector which detects the concentration of particulates suspended in a liquid.

BACKGROUND OF THE INVENTION

A known device detects the concentration of particulates in a liquid, for example, the concentration of soot suspended in engine lubricating oil from the light transmittance of the liquid, specifically, the amount of light transmitted through the liquid. The device includes a detection mechanism having a light emission unit and a light reception unit. The light emission unit emits light toward the liquid, and the light reception unit detects the amount of light transmitted through the liquid. Some of the light emitted from the light emission unit is absorbed and scattered by the particulates suspended in the liquid. Thus, the transmitted light amount detected by the light reception unit corresponds to the amount of particulates suspended in the liquid. Accordingly, the particulate concentration may be detected from the transmitted light amount.

In the detection mechanism described above, when a detection surface contacting the liquid that is subject to detection is stained, the detected amount of light decreases. This lowers the detection accuracy of the particulate concentration.

To solve this problem, for example, patent publication 1 describes a device including a detection mechanism arranged in an oil pan for an engine. The detection mechanism includes a float that floats and pitches on the surface of the oil. The pitching motion of the float is used to clean the detection surface of the detection mechanism.

In the device described in patent document 1, the surface level of the oil changes before and after the engine starts running. This produces the pitching motion of the float. Thus, when the amount of the oil in the oil pan decreases, the pitching range of the float is narrowed. This narrows the range of the detection surface that is cleaned. Such a problem that occurs when the oil amount decreases may be solved, for example, by determining the position at which the float is arranged taking into consideration the surface level when the oil amount decreases. However, such a solution would lead to a further problem. Specifically, when there is a sufficient amount of oil, the float would be immersed in the oil and constantly be floating upward. Thus, it would be difficult for the pitching motion of the float to be produced.

In this manner, the prior art device cannot properly remove stains from the detection surface.

[Patent Document 1] Japanese Laid-Open Patent Publication No. 8-86751

SUMMARY OF THE INVENTION

It is an object of the present invention to provide a particulate concentration detector that removes stains from a detection surface in a desirable manner.

To achieve the above object, one aspect of the present invention provides a particulate concentration detector including a detection mechanism having a light emission unit and a light reception unit. The light emission unit emits light from a light emission surface toward a liquid. The light reception unit receives the light from the light emission unit through the liquid with a light reception surface and detects the amount of light transmitted through the liquid. The particulate concentration detector detects the concentration of particulates suspended in the liquid from the amount of light detected by the detection mechanism. The detection mechanism includes a first light transmission unit, a second light transmission unit, a liquid chamber, and a third light transmission chamber. The first transmission unit is arranged at a location facing toward the light emission surface of the light emission unit. The second light transmission unit is arranged at a location facing toward the light reception surface of the light reception unit. The liquid chamber is formed between the first light transmission unit and the second light transmission unit and allows the liquid to flow therein. The third light transmission unit is arranged in an oscillatable manner in the liquid chamber so as to face toward the first light transmission unit and the second light transmission unit.

DETAILED DESCRIPTION OF THE PREFERRED EMBODIMENTS

A first embodiment of a particulate concentration detector according to the present invention will now be discussed with reference to FIGS. 1 to 4.

Figure 1:
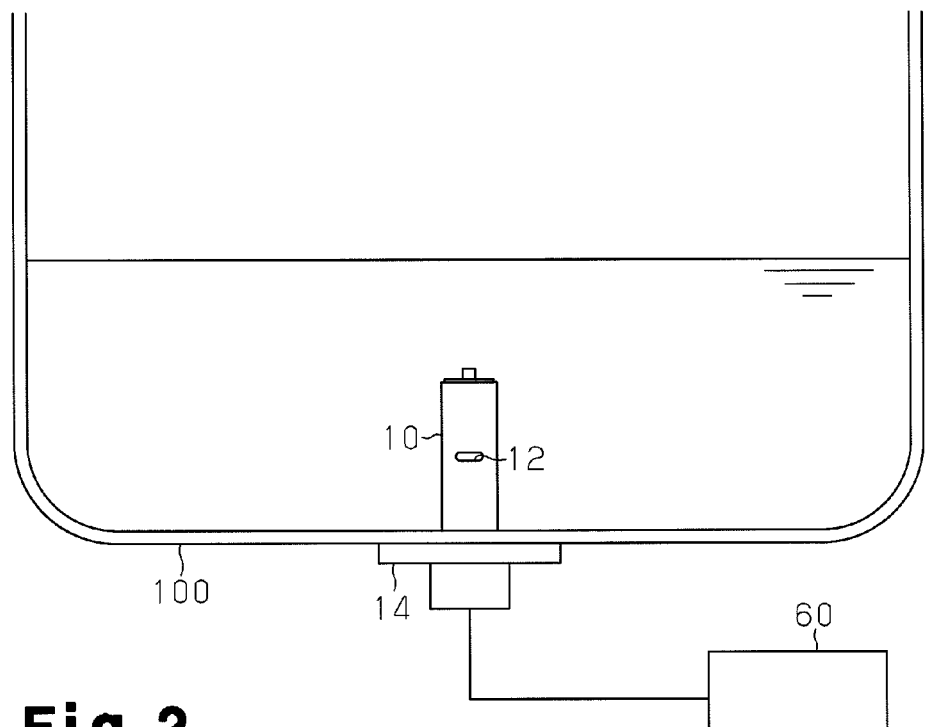
FIG. 1 is a schematic diagram showing a first embodiment of a particulate concentration detector according to the present invention.

The particulate concentration detector of FIG. 1 detects the concentration of particulates (soot and etc.) suspended in an engine lubricating oil, which serves as a detection subject liquid, from the amount of light transmitted through the lubricating oil.

As shown in FIG. 1, the particulate concentration detector includes a detection mechanism 10 and a computer 60.

The detection mechanism 10 is arranged in an engine oil pan 100 on its bottom surface. In the present embodiment, the oil pan 100 forms a container for containing a liquid. A housing 14, which is for fixing the detection mechanism 10, is arranged on the bottom surface outside the oil pan 100. The detection mechanism 10 outputs a detection signal, which is processed by the computer 60.

Figure 2:
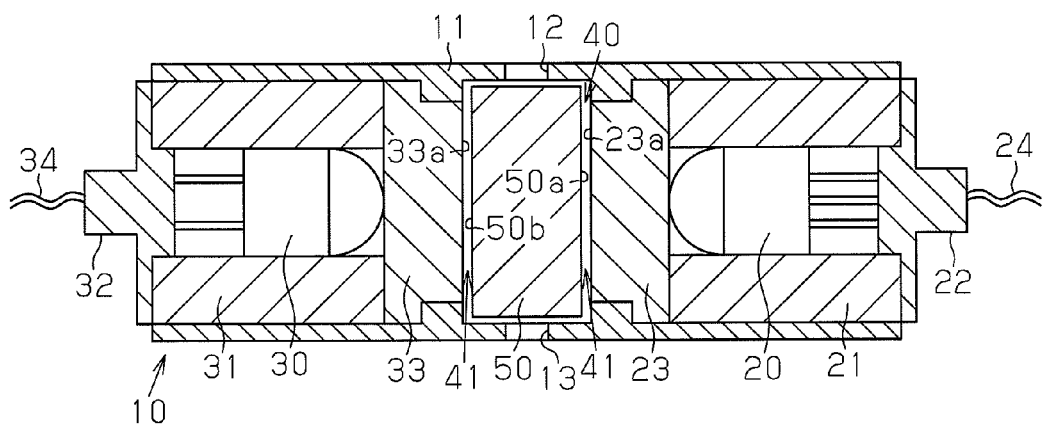
FIG. 2 is a cross-sectional view of a detection mechanism shown in FIG. 1.

As shown in FIG. 2, a holder 11, which forms the main body of the detection mechanism 10, has a generally box-like form.

The holder 11 has a first end portion in which a light emission unit 20, which emits light, is arranged. The light emission unit 20 is fixed to the holder 11 by a light emission unit holder 21. A light emission unit cap 22 is arranged on the light emission unit 20 on the opposite side of a light emission surface. An input terminal of the light emission unit 20 is fixed to the light emission unit cap 22, which prevents the light emission unit 20 from being exposed to the lubricating oil. A signal line 24 is arranged in the light emission unit cap 22 and connected to the input terminal of the light emission unit 20. The signal line 24 is connected to the computer 60 via the housing 14.

The holder 11 has a second end portion in which a light reception unit 30, which receives light from the light emission unit 20, is arranged facing toward the light emission unit 20. The light reception unit 30 is also fixed to the holder 11 by a light reception holder 31. A light reception unit cap 32 is arranged on the light reception unit 30 on the opposite side of a light reception surface. An output terminal of the light reception unit 30 is fixed to the light reception unit cap 32, which prevents the light reception unit 30 from being exposed to the lubricating oil. A signal line 34 is arranged in the light reception unit cap 32 and connected to the output terminal of the light reception unit 30. The signal line 34 is also connected to the computer 60 via the housing 14.

The light emission unit 20 includes a visible light element, which emits visible light having a wavelength of 670 nm, and an infrared light element, which emits infrared light having a wavelength of 890 nm. In the present embodiment, LEDs (light-emitting diodes) are used as such elements.

The light reception unit 30 includes a light reception element that outputs a signal in accordance with the amount of light emitted from the visible light element or the amount of light emitted from the infrared element. In the present embodiment, a photodiode of which output voltage becomes higher as the amount of received light increases is used as the light reception element.

A first light guide 23, which is fixed to the holder 11, is arranged at a location facing toward the light emission surface. A second light guide 33, which is fixed to the holder 11, is arranged at a location facing toward the light reception surface. The first light guide 23 and the second light guide 33 are formed from a material having a small light attenuation rate, for example, a light transmissive member such as silica glass. The first light guide 23 forms a first light transmission portion, and the second light guide 33 forms a second light transmission portion.

A tetragonal void defined between the first light guide 23 and the second light guide 33 in the holder 11 forms a liquid chamber 40. The liquid chamber 40 is in communication with the exterior of the holder 11 through holes 12 and 13 formed in the holder 11. The holes 12 and 13 allow lubricating oil to flow into the liquid chamber 40 from the exterior of the holder 11 or flow out of the liquid chamber 40 to the exterior of the holder 11. The liquid chamber 40 is filled with lubricating oil from the oil pan 100.

A third light guide 50 is arranged facing toward the first light guide 23 and the second light guide 33 in the liquid chamber 40. The third light guide 50 is block-shaped and formed from the same material as the first light guide 23.

Further, the third light guide 50 has an outline that is slightly smaller than the liquid chamber 40 so as to allow the third light guide 50 to oscillate in the liquid chamber 40. The third light guide 50 forms a third light transmission member.

In the liquid chamber 40, a clearance between the first light guide 23 and the third light guide 50 and a clearance between the second light guide 33 and the third light guide 50 form a channel into which lubricating oil flows. The light reception unit 30 detects the amount of light transmitted through the lubricating oil that flows through the channel 41. The two surfaces of the first light guide 23 and third light guide 50 facing toward each other and the two surfaces of the second light guide 33 and the third light guide 50 facing toward each other form detection surfaces that come into contact with the lubricating oil, which is a detection subject. More specifically, the surface of the first light guide 23 facing toward the third light guide 50 defines a first detection surface 23a, the surface of the third light guide 50 facing toward the first light guide 23 defines a second detection surface 50a, the surface of the third light guide 50 facing toward the second light guide 33 defines a third detection surface 50b, and the surface of the second light guide 33 facing toward the third light guide 50 defines a fourth detection surface 33a.

The computer 60 is formed in a manner centered about a microcomputer, which includes a central processing unit (CPU), a read-only memory (ROM) pre-storing various types of programs, maps, etc., a random-access memory (RAM) temporarily storing computations results etc. of the CPU, an input interface, and an output interface. The computer 60 receives output signals from the light reception unit 30 of the detection mechanism 10 and performs a computation process on the signal to calculate the particulate concentration in the lubricating oil.

The calculation of the particulate concentration C of the lubricating oil performed by the computer 60 will now be described with reference to FIG. 3.

Generally, the deterioration of engine lubricating oil results in the suspension of particulates in the lubricating oil. Particulate components include carbonyl and nitro groups, a benzene core, sulfates, soot, and abrasive grains. The component ratio of the particulates changes in accordance with the lubricating oil type, engine type, engine running state, deterioration progress of the lubricating oil, etc. The carbonyl and nitro groups have a brownish red color. The benzene core, sulfate, soot, and abrasive grains have a black color. Thus, the lubricating oil has a different color when the component ratio is different.

The light entering the lubricating oil is transmitted through the liquid without striking particulates of a sludge precursor or transmitted through the liquid as it strikes particulates and becomes multiply scattered. Visible light has a characteristic in which it is absorbed by particulates when multiply scattered. Infrared light has a characteristic in which it is not absorbed by particulates when multiply scattered. The absorption rate of the visible light differs depending on the color of the particulates.

Figure 3:
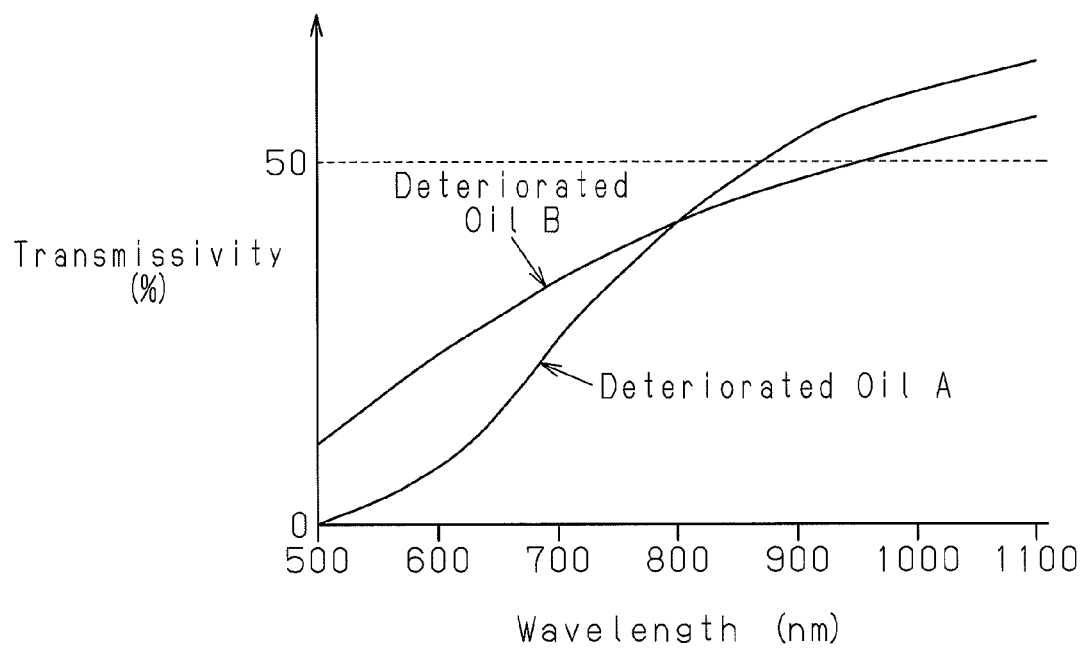
FIG. 3 is a graph showing the relationship of light transmission rate and light wavelength for two types of deteriorated oils having different particulate component ratios.

FIG. 3 shows the relationship of light transmission rate and light wavelength for two types of deteriorated oils having different particulate component ratios. The transmission rate is a value defined by the ratio of the light emission amount of the light emission unit and the light reception amount of the light reception unit (light reception amount of light reception unit/light emission amount of light emission unit×100(%)) and becomes smaller as the particulate concentration becomes higher. As shown in FIG. 3, in the visible light range, the transmission rate of deteriorated oil A is less than the transmission rate of deteriorated oil B. In the infrared light range, the transmission rate of the deteriorated oil A is greater than the transmission rate of the deteriorated oil B. It is thus apparent that the relationship in the level of the transmission rate changes in accordance with the wavelength of the inspection light. The visible light range transmission rate of the deteriorated oil A is smaller than that of the deteriorated oil B. Therefore, it is believed that deteriorated oil A includes a large amount of particulates functioning as light absorption components, for example, black particulates.

As described above, the component ratio of particulates in the lubricating oil affects the scattered amount and absorbed amount of light in the lubricating oil. Accordingly, even if the amount of particulates suspended in the lubricating oil is the same, that is, even if the particulate concentration is the same, the transmitted light amount differs if the component ratio of the particulates differs. Thus, the detection of the particulate concentration based on the transmitted light amount allows for the detection of the particulate concentration in a simpler manner in comparison to a particulate concentration measurement process that performs centrifugal separation or the like. However, the detection of the particulate concentration based on the transmitted light amount tends to be affected by the particulate component ratio and is therefore inferior in terms of detection accuracy. In the present embodiment, lights of different wavelengths emitted from the light emission unit 20 are used to detect the transmitted light amount of the lubricating oil in each wavelength. Then, the light transmission rate for each wavelength calculated from the transmitted light amount is used to detect the particulate concentration. This suppresses detection errors in the particulate concentration resulting from the component ratio of the particulates suspended in the oil.

A visible light transmission rate T1, which is the transmission rate when the visible light element of the light emission unit 20 emits light, and an infrared light transmission rate T2, which is the transmission rate when the infrared light element of the light emission unit 20 emits light, are calculated from the next equations (1) and (2).

visible light transmission rate $T1$=visible light transmission amount $I1$/visible light emission amount $Io1 \times 100$(%)     (1)

infrared light transmission rate $T2$=infrared light transmission amount $I2$/infrared light emission amount $Io2 \times 100$(%)     (2)

The visible light transmission amount I1 is the amount of visible light transmitted through the lubricating oil and is detected in the light reception unit 30. The visible light emission amount Io1 is the amount of light emitted from the visible light element of the light emission unit 20 and is a preset value. In a similar manner, the infrared light transmission amount I2 is the amount of infrared light transmitted through the lubricating oil and is detected in the light reception unit 30. The infrared light emission amount Io2 is the amount of light emitted from the visible light element of the light emission unit 20 and is a preset value.

When using the Lambert-Beer law to express the transmissivity of light in a liquid with a light absorption term and a light scattering term, the next equation (3) is obtained.

$$Ln(1/T) = \{\epsilon(\lambda) \times C \times L\} + \{G(\lambda) \times C \times L\} \quad (3)$$

Ln: natural logarithm
T: transmissivity of light in a liquid
$\epsilon(\lambda)$: absorption coefficient of particulates in light wavelength $\lambda$
$G(\lambda)$: attenuation coefficient of particulates in light wavelength $\lambda$
C: particulate concentration
L: optical path length In equation 3, the term "$\{\epsilon(\lambda) \times C \times L\}$" is the absorption term, and "$\{G(\lambda) \times C \times L\}$" is the scattering term.

The visible light from the visible light element irradiating the lubricating oil is categorized into a scattering component, an absorption component, and a transmission component. Accordingly, the visible light transmissivity T1 is expressed by the next equation (4) based on equation (3).

$$Ln(1/T1) = \{\epsilon(670) \times C \times L\} + \{G(670) \times C \times L\} \quad (4)$$

T1: transmissivity when irradiating lubricating oil with light at wavelength 670 nm (=visible light transmission amount I1/visible light emission amount $Io1 \times 100$)
$\epsilon(670)$: absorption coefficient of particulates in light at wavelength 670 nm
$G(670)$: attenuation coefficient of particulates in light at wavelength 670 nm The infrared light from the infrared light element irradiating the lubricating oil is categorized into a scattering component and a transmission component. Accordingly, the infrared light transmissivity T2 is expressed by the next equation (5) based on equation (3).

$$Ln(1/T2) = \{G(890) \times C \times L\} \quad (5)$$

T2: transmissivity when irradiating lubricating oil with light at wavelength 890 nm (=infrared light transmission amount I2/infrared light emission amount $Io2 \times 100$)
$G(890)$: attenuation coefficient of particulates in light at wavelength 890 nm The difference between equation (4) and equation (5) is obtained and the particulate concentration C is analyzed. This obtains the next equation (6).

$$Ln\left(\frac{1}{T1}\right) - Ln\left(\frac{1}{T2}\right) = \quad (6)$$

$$\{\epsilon(670) \times C \times L + G(670) \times C \times L\} - \{G(890) \times C \times L\}$$

$$C = -1 \times \frac{1}{L \times \{\epsilon(670) + G(670) - G(890)\}} \times Ln\left(\frac{T1}{T2}\right)$$

where when $\alpha = \frac{1}{L \times \{\epsilon(670) + G(670) - G(890)\}}$ is satisfied, $$C = -\alpha \times Ln\left(\frac{T1}{T2}\right)$$

As shown by equation (6), the particulate concentration C is calculated from the logarithm of the ratio between the visible light transmissivity T1 and the infrared light transmissivity T2. This suppresses detection errors in the particulate concentration C resulting from the component ratio of the particulates suspended in the lubricating oil.

In the detection mechanism 10, lubricating oil comes into contact with the first light guide 23, the second light guide 33, and the third light guide 50. When the first detection surface 23a of the first light guide 23, the fourth detection surface 33a of the second light guide 33, or the second detection surface 50a and third detection surface 50b of the third light guide 50 are stained (by particulate components in the lubricating oil), the visible light transmission amount I1 and infrared light transmission amount I2 decrease and lower the detection accuracy of the particulate concentration C. In the detection mechanism 10 of the present embodiment, the third light guide 50 is set as described above. This reduces the staining of each detection surface.

In detail, the detection mechanism 10 is immersed in lubricating oil and the third light guide 50 is arranged so as to be oscillatable in the liquid chamber 40, which the lubricating oil is allowed to flow therein and thereout. As the lubricating oil enters and exits the liquid chamber 40 and the vibration of the engine is transmitted to the detection mechanism 10 via the oil pan 100, the third light guide 50 oscillates.

Figure 4A:
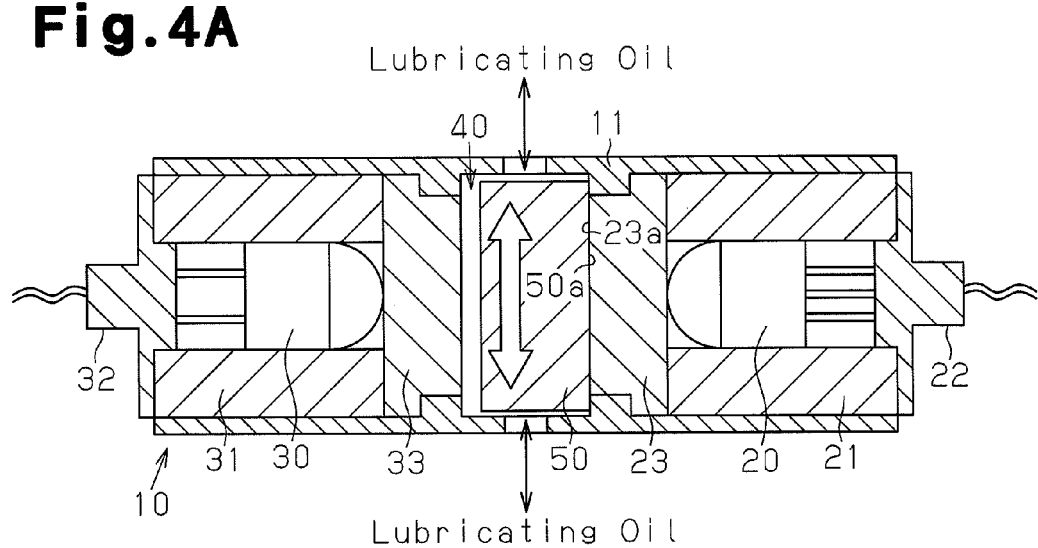
FIG. 4(a) is a cross-sectional view showing the cleaning of two detection surfaces of a first light guide and third light guide in a detection mechanism shown in FIG. 2.

As shown in FIG. 4(a), when the third light guide 50 is in contact with the first light guide 23, oscillation of the third light guide 50 slides the first detection surface 23a of the first light guide 23 along the second detection surface 50a of the third light guide 50. This scrapes off stains from the first detection surface 23a and second detection surface 50a.

Figure 4B:
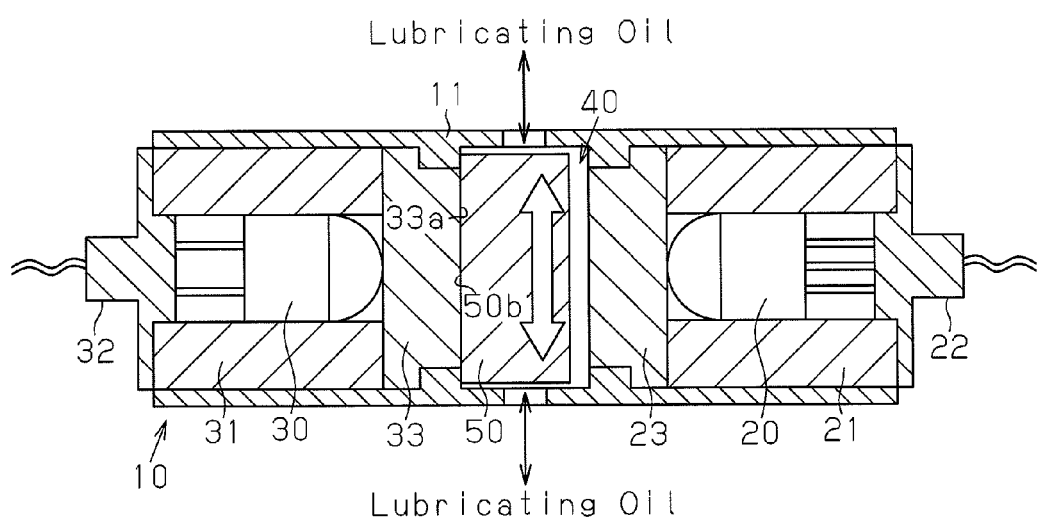
FIG. 4(b) is a cross-sectional view showing the cleaning of two detection surfaces of a second light guide and third light guide in the detection mechanism shown in FIG. 2.

In the same manner, as shown in FIG. 4(b), when the third light guide 50 is in contact with the second light guide 33, oscillation of the third light guide 50 slides the third detection surface 50b of the third light guide 50 along the fourth detection surface 33a of the second light guide 33. This scrapes off stains from the third detection surface 50b and fourth detection surface 33a.

The cleaning action of each detection surface produced by the oscillation of the third light guide 50 reduces stains from the first to fourth detection surfaces 23a, 50a, 50b, and 33a. This also prevents the detection accuracy of the particulate concentration C from being lowered by such stains.

In the prior art device that has been described in the prior art section, the detection mechanism must be set taking into consideration the positional relationship of the liquid level and float. However, the detection mechanism 10 may be set at any location as long as it is in the lubricating oil. Thus, the degree of freedom for the setting position of the detection mechanism 10 is high. This allows the detection mechanism 10 to be arranged on the bottom surface of the oil pan 100 as described above. The arrangement of the detection mechanism 10 on the bottom surface of the oil pan 100 maintains the third light guide 50 in an oscillatable state in the liquid chamber 40 even if the amount of lubricating oil in the oil pan 100 decreases for a certain extent. Accordingly, the stains on the detection surfaces (first to fourth detection surfaces 23a, 50a, 50b, and 33a) that come into contact with the lubricating oil are reduced in comparison with the prior art device.

Further, the detection mechanism 10 is fixed to the bottom surface of the oil pan 100. Thus, the detection mechanism 10 is kept immersed in the lubricating oil as much as possible even when the oil pan 100 is inclined relative to the oil level. This obtains the cleaning action produced with the third light guide 50 even when the oil pan 100 is inclined.

As described above, the present embodiment has the advantages described below.

(1) When the third light guide 50 is oscillated by the lubricating oil that enters and exits the liquid chamber 40, the first detection surface 23a of the first light guide 23 slides along the second detection surface 50a of the third light guide 50. This scrapes off stains from the detection surfaces 23a and 50a. In this same manner, the fourth detection surface 33a of the second light guide 33 slides along the third detection surface 50b of the third light guide 50 and scrapes off stains from the detection surfaces 33a and 50b. Such cleaning action of each detection surface produced by the oscillation of the third light guide 50 reduces stains from the first to fourth detection surfaces 23a, 50a, 50b, and 33a. This also prevents the detection accuracy of the particulate concentration C from being lowered by such stains.

The detection mechanism 10 of the present embodiment may be set at any location as long as it is in the lubricating oil. Thus, the degree of freedom for the setting position of the detection mechanism 10 is high. This allows the detection mechanism to be arranged near the bottom surface of the oil pan 100, which contains the lubricating oil. When arranging the detection mechanism 10 on the bottom surface of the oil pan 100, the third light guide 50 is maintained in an oscillatable state even if the amount of lubricating oil in the oil pan 100 decreases for a certain extent. This reduces stains from the first to fourth detection surfaces 23a, 50a, 50b, and 33a in a preferable manner.

(2) The detection mechanism 10 is fixed to the bottom surface of the oil pan 100, which contains the lubricating oil. Thus, the detection mechanism 10 is kept immersed in the lubricating oil as much as possible even when the oil pan 100 is inclined. This obtains the cleaning action produced with the third light guide 50 even when the oil pan 100 is inclined.

(3) The detection mechanism 10 is set in the oil pan 100 for the engine. Thus, the concentration of the particulates suspended in the engine lubricating oil may be detected. Further, the third light guide 50 may be oscillated by engine vibration.

A second embodiment of a particulate concentration detector according to the present invention will now be discussed with reference to FIGS. 5 to 7.

In the first embodiment, the third light guide 50 is a single body. In the present embodiment, a third light guide 80 includes a plurality of light guides 81 arranged next to one another along the direction of the optical path of the light emitted from the light emission unit 20, as shown in FIG. 5. The light guides 81 are also formed from the same material as the third light guide 50 of the first embodiment and have a block-shaped outline. In the same manner as the third light guide 50, the light guides 81 have an outline that is slightly smaller than the liquid chamber 40 so as to allow the light guide 81 to oscillate in the liquid chamber 40.

By forming the third light guide 80 from a plurality of segments as described above, the advantages described below are obtained.

Figure 6:
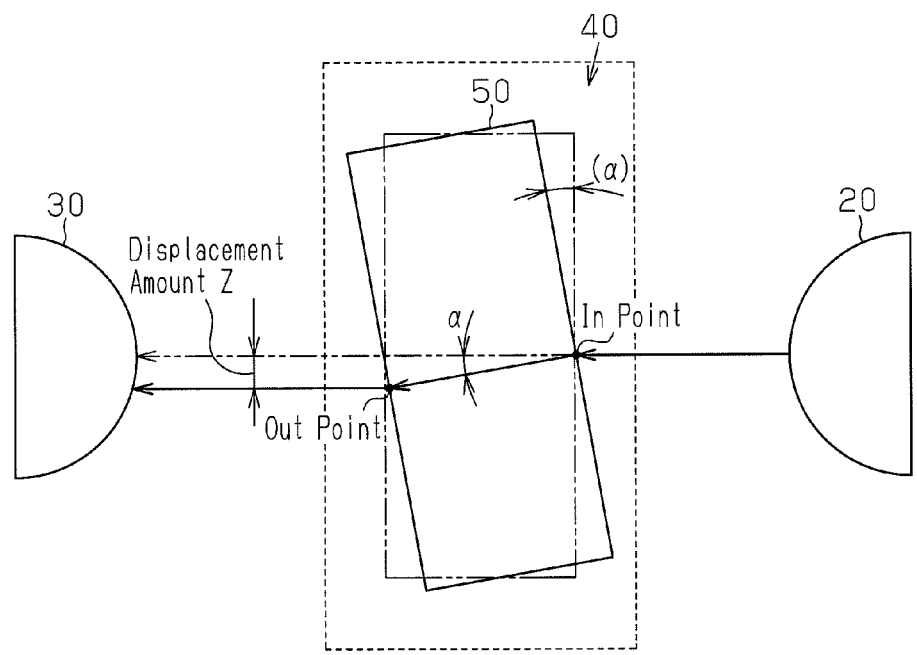
FIG. 6 is a schematic diagram showing displacement of an optical path when the third light guide of FIG. 2 is inclined.

The double-dashed lines in FIG. 6 show the third light guide 50 in a state in which it is not inclined to the direction of the optical path of the light emitted from the light emission unit 20 toward the light reception unit 30, that is in a state in which both the second detection surface 50a and the third detection surface 50b are perpendicular to the proceeding direction of the light. In this case, the light emitted from the light emission unit 20 reaches the light reception unit 30 without being refracted when transmitted through the third light guide.

The solid lines in FIG. 6 show the third light guide 50 in a state in which it is inclined to the direction of the optical path of the light emitted from the light emission unit 20 toward the light reception unit 30. In this case, the light emitted from the light emission unit 20 is refracted at the interface (second detection surface 50a) between the lubricating oil and third light guide 50 and then transmitted through the third light guide 50. The light is refracted again at the interface (third detection surface 50b) between the third light guide 50 and the lubricating oil. The light exits the lubricating oil from the third light guide 50 and proceeds toward the light reception unit 30.

When the third light guide 50 is inclined in such a manner, the optical path becomes displaced between the point (in point shown in FIG. 6) at which light enters the third light guide 50 and the point (out point shown in FIG. 6) at which light exits the third light guide 50. The displacement changes the light reception amount (transmitted light amount) of the light reception unit 30. Such displacement amount Z of the optical path is expressed by the next equation (7).

$$\text{displacement amount } Z = \text{optical path length } L \text{ in light guide} \times \sin \alpha \qquad (7)$$

The optical path length L in a light guide refers to the distance between two points, the in point and the out point. For example, in the third light guide 50, the optical length L refers to the transmission distance of the light transmitted through the third light guide 50. Further, "$\alpha$" is the value representing the refraction angle of the light refracted at the second detection surface 50a from the advancing direction of the light that would be transmitted through the third light guide 50 when not refracted at the second detection surface 50a.

As apparent from equation (7), the displacement amount Z increases as the inclination angle $\alpha$ of the third light guide 50 increases. Further, the displacement amount Z increases as the optical path length L of the third light guide 50 lengthens. The optical path L in the third light guide 50 lengthens as the thickness of the third light guide 50 in the direction light advances increases. Thus, the displacement amount Z increases as such thickness increases.

In the present embodiment, the third light guide 80 includes the plurality of light guides 81. This allows the thickness of each light guide 81 to have a smaller thickness than the third light guide 50, which is formed by a single body. Further, each of the light guides 81 is inclinable in a manner independent from one another. When the third light guide 50 formed by a single body and one of the two light guides 81 forming the third light guide 80 are, for example, inclined by the same inclination angle, a comparison in the displacement amount Z of the optical path would be as described below.

Figure 5:
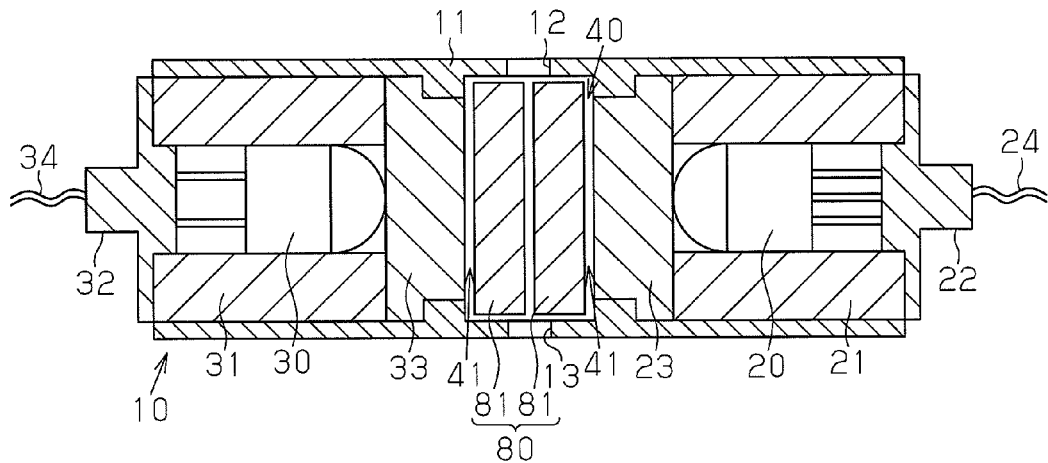
FIG. 5 is a cross-sectional view showing a detection mechanism in a second embodiment according to the present invention.
Figure 7:
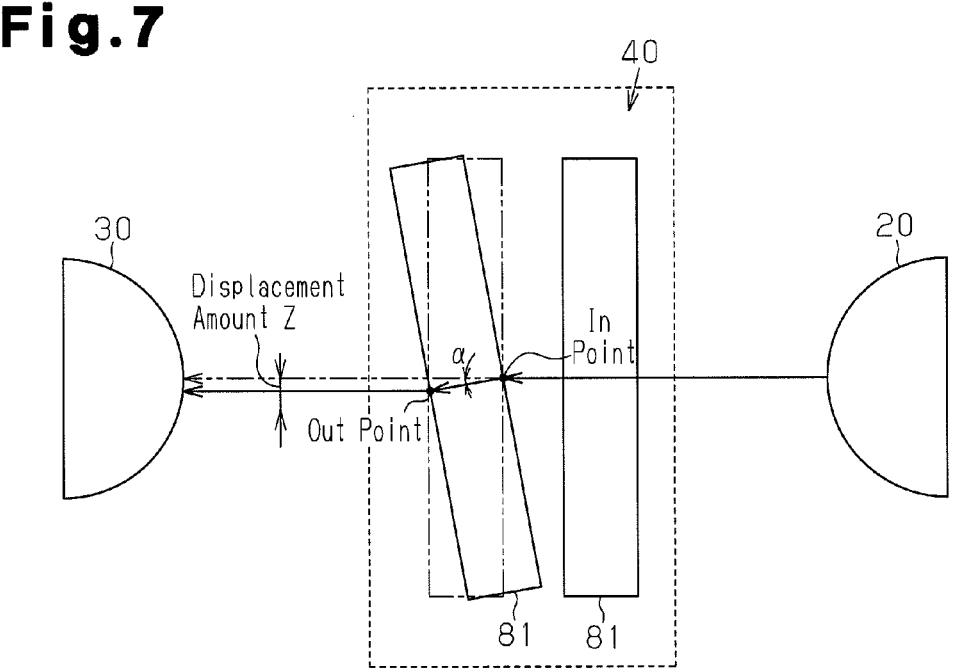
FIG. 7 is a schematic diagram showing displacement of an optical path when a third light guide of FIG. 5 is inclined.

As shown in FIGS. 7 and 5, each of the light guides 81 forming the third light guide 80 has a thickness that is smaller than the thickness of the third light guide 50 formed by a single body. This shortens the optical length L (distance between the two points, the in point and the out point out). Accordingly, as apparent from equation (7), each of the light guides 81 forming the third light guide 80 has a smaller displacement amount Z.

In the present embodiment, the light guides 81, which form the third light guide 80, are also oscillatable in the liquid chamber 40. Therefore, the same advantages as the first embodiment may be obtained.

Each of the above-described embodiments may be modified as described below.

Figure 8:
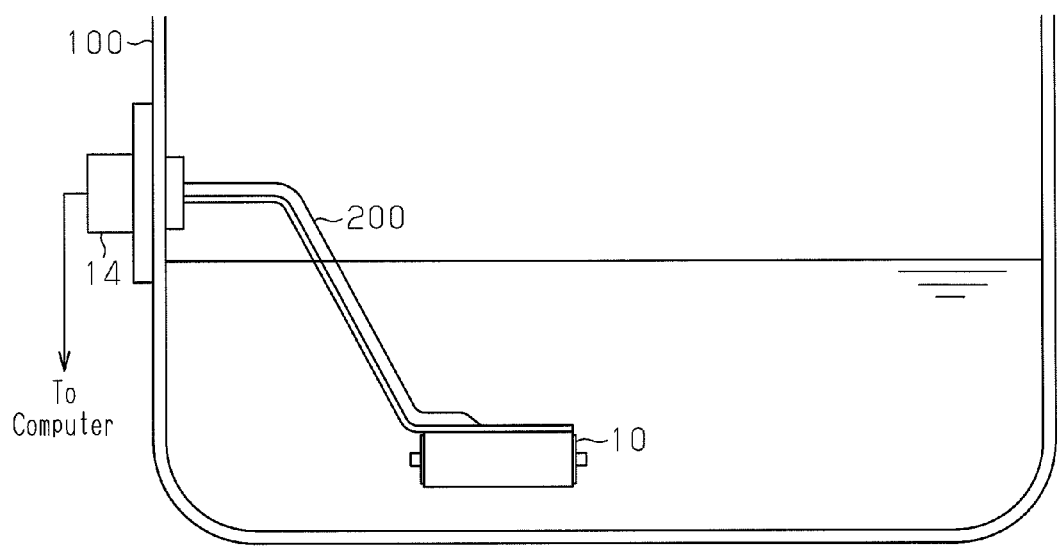
FIG. 8 is a schematic diagram showing a particulate concentration detector which is a modification of the first embodiment.

The detection mechanism 10 is fixed to the bottom surface of the oil pan 100. However, the detection mechanism 10 may be supported by a stay in the oil pan 100 so as to be located in the lubricating oil of the oil pan 100. For example, as shown in FIG. 8, a stay 200 may have a first end connected to a side surface of the oil pan 100 and a second end immersed in lubricating oil near the bottom surface of the oil pan 100, with the detection mechanism 10 being fixed to the second end of the stay 200. This modification also keeps the detection mechanism 10 in the lubricating oil as much as possible even when the oil pan 100 is inclined. Accordingly, the cleaning action may be produced with the third light guide 50 even during such an inclination. In this modification, the engine vibration amplified by the stay 200 is transmitted to the detection mechanism 10. This further easily oscillates the third light guide and improves the cleaning action.

In the first embodiment, lights of two different wavelengths are used. However, lights of three or more different wavelengths may be used. In such a case, for example, the particulate concentration is detected in the next manner. First, the transmitted light amount is measured for each of three lights having the wavelengths of A, B, and C to obtain the transmissivity for each wavelength from the measured transmitted light amount. In the same manner as the first embodiment, a particulate concentration C1 is obtained from the ratio of the transmissivities corresponding to the lights of wavelengths A and B, and a particulate concentration C2 is obtained from the ratio of the transmissivities corresponding to the lights of wavelengths A and C. Then, the average value of the particulate concentration C1 and the particulate concentration C2 is used as the final particulate concentration C.

In the first embodiment, the light emission unit 20 emits visible light having a wavelength of 670 nm and infrared light having a wavelength of 890 nm. However, light having other wavelengths may be used as long as detection errors resulting from the component ratio of the particulates suspended in the lubricating oil are suppressed when detecting the particulate concentration in the manner described in the first embodiment.

Instead of arranging the visible light element and the infrared light element in the sole light emission unit 20, a light emission unit including a visible light element and a light emission unit including an infrared light element may be used, with the light reception unit 30 receiving light from each of the light emission units. Further, a visible light emission unit including a visible light element, a visible light reception unit which receives light from the visible light emission unit, an infrared light emission unit including an infrared light emission unit, and an infrared light reception unit which receives light from the infrared light reception unit may be used.

Instead of emitting lights having different wavelengths from the light emission unit 20 and detecting the particulate concentration C from equation (6), the light emission unit 20 may emit one type of light and detect the particulate concentration C from the transmissivity of the light. In such a case, the detection errors resulting from the component ratio of the particulates suspended in the lubricating oil may not be suppressed. However, the particulate concentration C is detected in a simpler manner.

The third light guide 50 and the light guide 81 do not have to have a block-shaped form and may be changed as required.

In the above-described embodiments, the particulate concentration of the engine lubricating oil is detected. However, the present invention may be applied in the same manner to a detector that detects the particulate concentration of other liquids.

Instead of arranging the detection mechanism 10 in the oil pan 100 for the engine, the detection mechanism 10 may be arranged in a testing device that detects the concentration of particulates suspended in oil. In this case as well, the detection mechanism 10 is immersed in a detection subject liquid contained in a container, and a third light guide is oscillated by the movement of the detection subject liquid. Accordingly, the cleaning action is obtained.

The invention claimed is:

1. A particulate concentration detector comprising:
   a detection mechanism including a light emission unit, which emits light from a light emission surface toward a liquid, and a light reception unit, which receives the light from the light emission unit through the liquid with a light reception surface and detects the amount of light transmitted through the liquid, with the particulate concentration detector detecting the concentration of particulates suspended in the liquid from the amount of light detected by the detection mechanism, the detection mechanism including:
   a first light transmission unit arranged at a location facing toward the light emission surface of the light emission unit;

a second light transmission unit arranged at a location facing toward the light reception surface of the light reception unit;

a liquid chamber formed between the first light transmission unit and the second light transmission unit and allowing the liquid to flow therein and flow thereout; and a third light transmission unit arranged in an oscillatable manner in the liquid chamber so as to face toward the first light transmission unit and the second light transmission unit, wherein the third light transmission unit is oscillated by movement of the liquid in the liquid chamber or vibration of the detection mechanism.

2. The detector according to claim 1, wherein the detection mechanism detects the amount of light transmitted through the liquid that enters a channel formed by at least one of a clearance between the third light transmission unit and the first light transmission unit and a clearance between the third light transmission unit and the second light transmission unit.

3. The detector according to claim 1, wherein:
the first light transmission unit includes a first detection surface;
the second light transmission unit includes a fourth detection surface:
the third light transmission unit includes a second detection surface facing toward the first detection surface and a third detection surface facing toward the fourth detection surface; and
oscillation of the third light transmission unit slides the first detection surface along the second detection surface or slides the third detection surface along the fourth detection surface.

4. The detector according to claim 1, wherein the third light transmission unit includes a plurality of light transmission units arranged along an optical path direction of the light emitted from the light emission unit.

5. The detector according to claim 1, wherein the detection mechanism is fixed to a bottom surface of a container containing the liquid.

6. The detector according to claim 1, wherein the detection mechanism is supported in a container by a stay so as to be located in the liquid contained in a container.

7. The detector according to claim 1, wherein the detection mechanism is set in an oil pan for an engine.

8. The detector according to claim 2, wherein:
the first light transmission unit includes a first detection surface;
the second light transmission unit includes a fourth detection surface:
the third light transmission unit includes a second detection surface facing toward the first detection surface and a third detection surface facing toward the fourth detection surface; and
oscillation of the third light transmission unit slides the first detection surface along the second detection surface or slides the third detection surface along the fourth detection surface.

9. The detector according to claim 8, wherein the third light transmission unit includes a plurality of light transmission units arranged along an optical path direction of the light emitted from the light emission unit.

10. The detector according to claim 9, wherein the detection mechanism is fixed to a bottom surface of a container containing the liquid.

11. The detector according to claim 9, wherein the detection mechanism is supported in a container by a stay so as to be located in the liquid contained in a container.

12. The detector according to claim 9, wherein the detection mechanism is set in an oil pan for an engine.

13. The detector according to claim 2, wherein the third light transmission unit includes a plurality of light transmission units arranged along an optical path direction of the light emitted from the light emission unit.

14. The detector according to claim 13, wherein the detection mechanism is fixed to a bottom surface of a container containing the liquid.

15. The detector according to claim 13, wherein the detection mechanism is supported in a container by a stay so as to be located in the liquid contained in a container.

16. The detector according to claim 13, wherein the detection mechanism is set in an oil pan for an engine.

17. The detector according to claim 3, wherein the third light transmission unit includes a plurality of light transmission units arranged along an optical path direction of the light emitted from the light emission unit.

18. The detector according to claim 17, wherein the detection mechanism is fixed to a bottom surface of a container containing the liquid.

19. The detector according to 17, wherein the detection mechanism is supported in a container by a stay so as to be located in the liquid contained in a container.

20. The detector according to claim 17, wherein the detection mechanism is set in an oil pan for an engine.

* * * * *